United States Patent [19]
Balding

[11] Patent Number: 5,167,640
[45] Date of Patent: Dec. 1, 1992

[54] SYRINGE NEEDLE SHIELD

[76] Inventor: James G. Balding, 11925 Koenigstein, Santa Paula, Calif. 93060

[21] Appl. No.: 738,688

[22] Filed: Jul. 31, 1991

[51] Int. Cl.⁵ .............................................. A61M 5/32
[52] U.S. Cl. .................................. 604/192; 604/263
[58] Field of Search ................ 604/198, 263, 192, 187

[56] References Cited

U.S. PATENT DOCUMENTS

| | | | |
|---|---|---|---|
| 4,863,434 | 9/1989 | Bayless | 604/198 |
| 4,909,792 | 3/1990 | Norelli | 604/192 |
| 4,915,696 | 4/1990 | Feimer | 604/192 |
| 4,944,731 | 7/1990 | Cole | 604/263 X |

Primary Examiner—John D. Yasko
Attorney, Agent, or Firm—Robert M. Wallace

[57] ABSTRACT

A shield for a conventional hypodermic syringe needle is disclosed, including an elastic body, expandable to conform to the syringe barrel and slidable on the barrel, flexible arm means extending from the body and normally biased inwardly in a closed position and appropriate ends located on the arm means for shielding the needle of the syringe from accidental pricking.

5 Claims, 2 Drawing Sheets

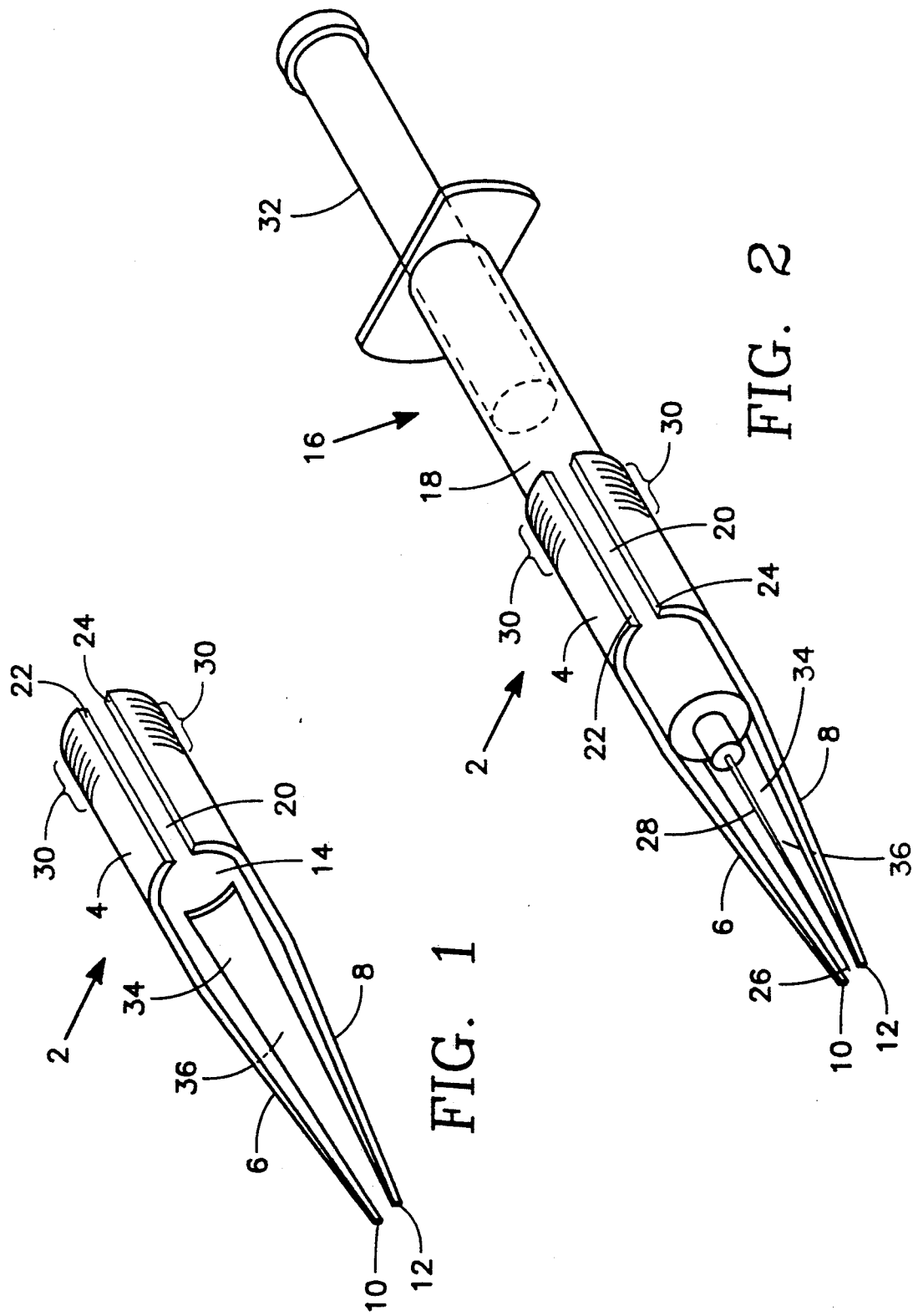

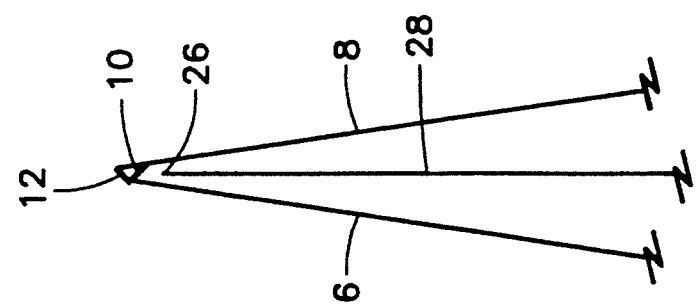
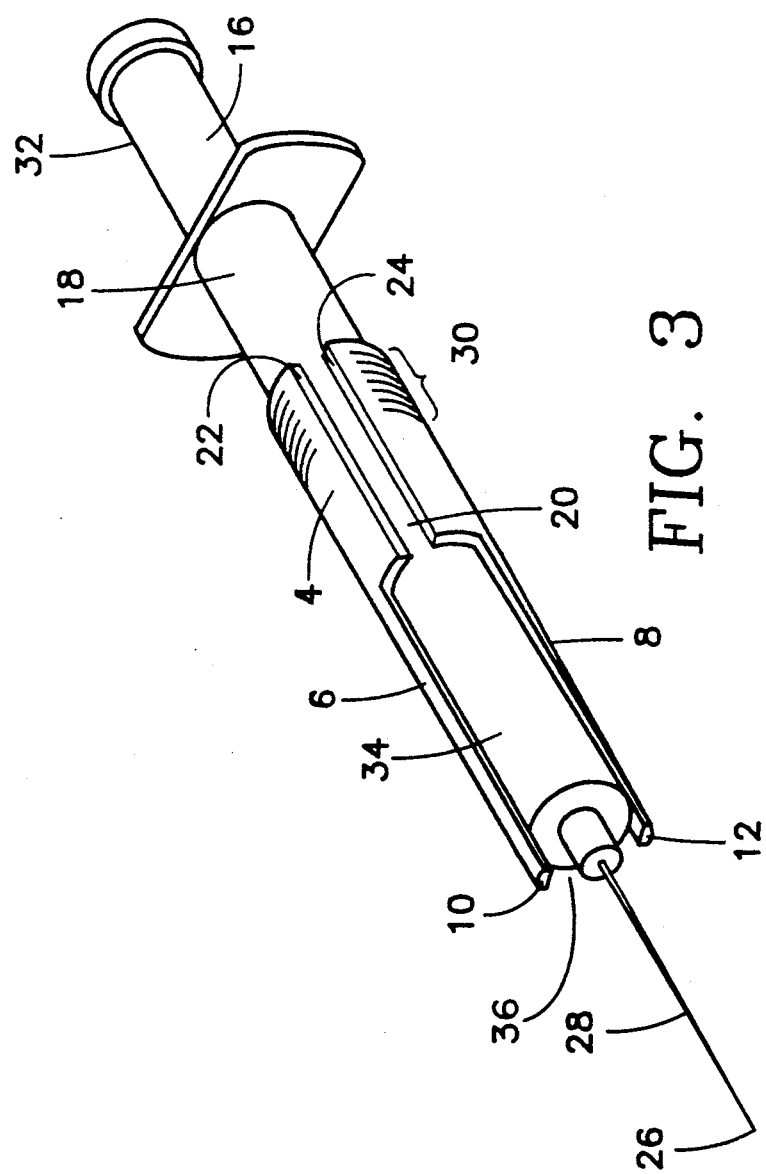
FIG. 3
FIG. 4

SYRINGE NEEDLE SHIELD

BACKGROUND OF THE INVENTION

The present invention relates to hypodermic syringes for withdrawing blood and administering serum and the like. More specifically, but without limitation, the present invention relates to a syringe needle shield that ma be an integral part of a syringe from the factory or may be retrofitted to a conventional syringe and operated with only one hand to shield the needle tip of the syringe from accidental pricking.

The need to protect against accidental pricking of a contaminated hypodermic needle is well known. The Acquired Immune Deficiency Syndrome (AIDS) disease has made the problem acute.

Several devices have been developed to prevent accidental pricking. One example of such a device discloses a slidable sheath with slots for receiving a knob on the syringe body. Tabs retain the sheath in a retracted or extended position.

Another example discloses a reclosable safety cap with two halves that covers or uncovers the needle by operating an external ring.

Still another device discloses a slidable guard with a single, spoon shaped shield member that may be extended or retracted to cover or uncover the needle tip.

However, none of the prior art devices provide an apparatus that may be either retrofitted or applicable to various sizes of existing syringe barrels; that can be easily operated by one hand; that place two or more barriers between the contaminated needle tip and a person's body; and that is simple and inexpensive to manufacture.

OBJECT OF THE INVENTION

It is therefore an object of the invention to provide a shield that may be retrofitted to various sizes of syringe barrels or that may be manufactured and/or supplied with the syringe.

It is a further object of the invention to provide an apparatus that can be operated with one finger (or thumb) of one hand.

It is still another object of the invention to provide an apparatus that puts at least two barriers between the contaminated needle tip and a person's body.

It is another object of the invention to provide an apparatus that is simple and inexpensive to manufacture.

SUMMARY OF THE INVENTION

Accordingly, the shield of the invention, adapted for use on a hypodermic syringe needle, includes an elastic body that is expandable to frictionally conform to the barrel of the syringe. A pair of first and second flexible elongated arms extend from the body and are biased inwardly for a normally closed position wherein the first arm being slightly shorter than the second arm, and the first arm having a slightly shorter arc length than the second arm, the second arm overlaps the first arm. Overlapping flanges or covers located on ends of each arm effectively shield the needle from accidental contact.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a perspective view of the invention including the body, elongated arms, ends and slot.

FIG. 2 is a perspective view of the invention in the extended or closed position frictionally installed and adapted to the barrel of a conventional hypodermic syringe.

FIG. 3 is a perspective view of the invention frictionally installed in the retracted or open position on the barrel of a conventional hypodermic syringe.

FIG. 4 is a perspective view of an alternative embodiment of the ends that shield the syringe needle tip.

DESCRIPTION OF A PREFERRED EMBODIMENT

The preferred embodiment of the invention is illustrated by way of example in FIGS. 1 to 3. As shown in FIG. 1, the shield 2 includes a body 4, elongated arms 6 and 8 and ends 10 and 12. Inner surface 14 of body 4 is shaped to substantially conform to barrel 18 of a typical syringe 16 when shield 2 is frictionally installed on barrel 18 as shown in FIGS. 2 and 3. Slot 20 extends along the entire length of body 4. In this way, body 4 may be elastically expanded from a "natural" or "non-expanded" state, as shown in FIG. 1, to an expanded state as shown in FIGS. 2 and 3. When expanded, shield 2 may be slidably installed over needle 28 and onto barrel 18, thus providing a positive yet frictionally slidable grip between inner surface 14 and barrel 18. Tabs 22 and 24 are provided to facilitate expanding body 4 for installation on barrel 18.

Once installed, shield 2 may be selectively positioned by sliding body 4 along the length of barrel 18 with use of but one hand.

Elongated arms 6 and 8 extend from opposite sides of body 4 and terminate in ends 10 and 12 respectively. Each arm has the same curvature as body 4, however, the arc length of arm 6 is less than the arc length of arm 8 and arm 6 is slightly shorter than arm 8. Arms 6 and 8 are normally biased in a "closed" position wherein end 10 abuts end 12. Thus, when shield 2 is installed on barrel 18 or a syringe 16 and positioned in the extended position, as shown in FIG. 2, ends 10 and 12 will both be positioned over tip 26 of needle 28 wherein end 10 is adjacent tip 26 and end 12 is adjacent end 10. Tip 26 is thus shielded by overlapping ends 10 and 12. In order to rearwardly position shield 2 on barrel 18, it is necessary to manually spread apart arms 6 and 8. It should be noted that, for clarity purposes only, FIGS. 1 and 2 do not show ends 10 and 12 completely "closed" over tip 26.

In operation, shield 2 is first expanded and then slidably installed on barrel 18 as previously described. Shield 2 is then rearwardly positioned on barrel 18, as shown in FIG. 3, by applying a rearwardly directed force on finger grips 30 causing arms 6 and 8 to spread apart and effectively separate ends 10 and 12, thereby exposing needle 28. Shield 2 is therefore held in place due to the frictional grip between body 4 and barrel 18. It should be noted that the forward and rearward movement of shield 2 on barrel 18 may be accomplished by a single finger or thumb of one hand thereby freeing the other hand, for example, to hold a patient from moving. Syringe 16 may then be conventionally filled by operating plunger 32 and a "shot" may then be administered in the usual fashion. It should be noted that when shield 2 is in the rearward position, as shown in FIG. 3, barrel 18 may be grasped by the fingers through openings 34 and 36 without impairment. In addition, openings 34 and 36 allow the fluid and fluid level in barrel 18 to be observed. After a shot is administered, shield 2 may be slidably positioned by one hand, as shown in FIG. 2, so that the now contaminated tip 26 is covered and isolated from an accidental contact with a person.

An alternative embodiment of ends 10 and 12 is shown in FIG. 4. As can be seen bent, ends 10 and 12 are formed in arms 6 and 8 respectively at an angle of less than 90 degrees. As a result, bent end 10 and arm 6 will be located within the angle formed by bent end 12 and arm 10. In this way, arms 6 and 8 lock together over needle tip 26. When an increasing force is applied by tip 26, arms 6 and 8 lock tighter together, the wedge shaped tip formed by arm 6 and bent end 10 being driven into the wedge shaped cup formed by arm 8 and bent end 12.

Although it is of little consequence to the invention, the invention may be fabricated in one piece from flexible plastic, glass, rubber or metal strips, or other suitable material.

While the present invention has been disclosed in connection with the preferred embodiment thereof, it should be understood that there may be other embodiments which fall within the spirit and scope of the invention as defined by the following claims.

I claim:
1. A shield for hypodermic syringe having a barrel and a needle comprising:
   a) an elastic body, expandable to conform to said syringe barrel and slidable on said barrel;
   b) flexible arc shaped arm means comprising first and second arms extending from said body, said arm means normally biased inwardly in a closed position, wherein the arc of said arm means has generally the same arc as said body;
   c) overlapping means disposed on said arm means for shielding said needle;
   d) a slot along said body, the slot allowing said body to be expanded for installing on said barrel;
   e) finger grips on said body, wherein said first arm is shorter than said second arm.
2. The apparatus defined in claim 1, wherein the arc length of said first arm is shorter than the arc length of said second arm.
3. The apparatus defined in claim 2, further including tabs.
4. The apparatus defined in claim 3, wherein the shielding means are perpendicular to said arms.
5. The apparatus defined in claim 3, wherein the shielding means form an angle less than 90 degrees to said arm.

* * * * *